(12) United States Patent
Heiler et al.

(10) Patent No.: US 6,323,165 B1
(45) Date of Patent: Nov. 27, 2001

(54) COMPOSITION AND METHOD FOR INHIBITING OF PROTEIN ON CONTACT LENS

(75) Inventors: David J. Heiler, Avon; Stephen E. Maier, Brockport; Susan P. Spooner, Rochester, all of NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 0 days.

(21) Appl. No.: 09/558,436

(22) Filed: Apr. 25, 2000

Related U.S. Application Data

(62) Division of application No. 08/846,403, filed on Apr. 30, 1997, now Pat. No. 6,096,138.
(60) Provisional application No. 60/017,864, filed on May 13, 1996.

(51) Int. Cl.[7] ................................ B08B 3/08; C11D 3/37
(52) U.S. Cl. ................. 510/112; 510/113; 510/114; 510/115; 514/839; 514/840; 134/42
(58) Field of Search ..................... 510/115, 113, 510/112, 1, 114; 424/78.04, 78.26, 78.08; 134/27, 30, 42, 26; 514/57, 839, 840; 252/179

(56) References Cited

U.S. PATENT DOCUMENTS

| | | | |
|---|---|---|---|
| 4,168,112 | * | 9/1979 | Ellis et al. . |
| 4,321,261 | * | 3/1982 | Ellis et al. . |
| 4,361,548 | * | 11/1982 | Smith et al. . |
| 4,388,229 | | 6/1983 | Fu .......................... 252/549 |
| 4,414,127 | | 11/1983 | Fu .......................... 252/95 |
| 4,436,730 | * | 3/1984 | Ellis et al. . |
| 4,443,429 | * | 4/1984 | Smith et al. . |
| 4,758,595 | * | 7/1988 | Ogunbiyi et al. . |
| 4,820,352 | | 4/1989 | Riedhammer et al. ................ 134/30 |
| 5,096,607 | * | 3/1992 | Mowrey-McKee et al. . |
| 5,422,073 | * | 6/1995 | Mowrey-McKee et al. . |
| 5,630,884 | * | 5/1997 | Huth . |

FOREIGN PATENT DOCUMENTS

| | | | |
|---|---|---|---|
| 0456467-A2 | 11/1991 | (EP) ................................ A61L/2/00 |
| WO98/04496 | * | 2/1998 | (FR) . |
| WO99/24543 | * | 5/1999 | (US) . |
| 94/13774 | | 6/1994 | (WO) .............................. C11D/3/37 |
| 95/00618 | | 6/1994 | (WO) .............................. C11D/3/00 |
| 95/09905 | | 4/1995 | (WO) .............................. C11D/3/37 |

OTHER PUBLICATIONS

"The Relative Toxicity of Five Common Disinfecting/Preserving Agents as Determined by a Modified Neutral Red Dye Release Assay and the Agar Overlay Technique" John F. Hamberger, MA, Christopher A. Root, BS, and David A Porter, PhD, ICLC, vol. 19 at 130–135, May/Jun. 1992.

* cited by examiner

Primary Examiner—Yogendra N. Gupta
Assistant Examiner—Gregory E. Webb
(74) Attorney, Agent, or Firm—Robert B. Furr, Jr.

(57) ABSTRACT

The invention is directed to compositions and methods used as in-the-eye and/or out-of-eye inhibitors of proteinaceous deposits on hydrophilic contact lenses. Compositions of the present invention comprise moderately charged polyquaternium polymers that selectively bind to hydrophilic contact lenses to block the binding of proteinaceous materials. Compositions of the present invention may be used in multipurpose cleaning solutions for contact lenses and can eliminate the need for special enzyme cleaners and the like for removing proteinaceous materials.

12 Claims, No Drawings

COMPOSITION AND METHOD FOR INHIBITING OF PROTEIN ON CONTACT LENS

This is a Divisional Application of U.S. Ser. No. 08/846,403 filed on Apr. 30, 1997 now U.S. Pat. No. 6,096,138, which claims the benefit of U.S. Provisional Application No. 60/017,864, filed May 13, 1996.

FIELD OF THE INVENTION

This invention relates to compositions and methods useful for inhibiting the deposition of protein and similar debris on contact lenses. In particular, moderately charged polyquaternium polymers have been found to both inhibit protein deposition on hydrophilic contact lenses and to be ophthalmologically safe for in-the-eye use in a contact-lens solution.

BACKGROUND OF THE INVENTION

During wear, contact lenses are susceptible to the accumulation of proteinaceous materials that may adhere to the surface of the lens. Proteinaceous materials include, for example, lysozyme, lactoferrin, albumin, and mucoproteins, all constituents of lachrimal tears. Contact lenses that are repeatedly worn over an extended period of time must be cleaned to remove these materials as part of a routine care regimen.

Particularly if contact lenses are not properly cleaned, lysozyme, mucoproteins, and the like can accumulate on the lenses and may lead to the lens wearer experiencing discomfort or a loss of visual acuity. The presence of proteinaceous deposits on the lens may also decrease gas permeability of the lenses or adversely affect the spectral characteristics of the lenses, Finally, proteinaceous deposits may interfere with the efficient sterilization of contact lenses.

Daily cleaning and/or disinfecting compositions or techniques now in predominant use on contact lenses do not prevent the accumulation of protein deposits over an extended period of time. In fact, one method of disinfecting, heat sterilization, may aggravate the problem by denaturing and precipitating proteinaceous materials onto the lens. Consequently, special cleaning compositions and techniques are in widespread use for removing the accumulation of protein deposits that cannot be adequately prevented by daily cleaning.

Accordingly, the cleaning of contact lenses is conventionally accomplished with one or both of two general classes of cleaners. Surfactant cleaners, generally known as "daily cleaners" because of their recommended daily use, are effective for the removal of most carbohydrate and lipid-derived matter. However, such cleaners are not as effective for removal of proteinaceous matter such as lysozyme. Typically, proteolytic enzymes derived from plant, animal, or microbial sources are used to remove the proteinaceous deposits. These "enzyme cleaners" are typically recommended for weekly use. Commonly, enzyme cleaners are employed by dissolving enzyme tablets in suitable aqueous solutions. See, for example, U.S. Pat. No. 5,096,607 to Mowrey-McKee et al. Other chemical agents that remove protein deposits have been developed. For example, U.S. Pat. No. 4,414,127 to Fu discloses compositions comprising metal chloride catalysts in combination with a peroxide that chemically degrade and remove proteinaceous deposits.

In addition to the use of proteolytic enzymes or other chemical agents that degrade protein, contact lens wearers may need to rub the contact lenses (typically between the forefinger and palm) during daily cleaning of contact lenses. This is usually required or recommended to retard the build-up of protein deposits that will eventually require an enzyme cleaner or other special cleaner for removing protein deposits.

Special cleaners and procedures for removing or degrading proteins are clearly an extra burden for contact-lens wearers, and the necessity for frequent "rubbing and cleaning" of contact lenses add to the time and effort involved in the daily care of contact lenses. Many contact lens wearers do not like the burden of having to perform a daily "rubbing and cleaning" regimen. Some wearers may even be negligent in the proper "rubbing and cleaning" regimen, which may result in contact-lens discomfort and other problems.

The deposition of proteinaceous materials can also cause adverse affects or limit the life of so-called planned replacement lenses (PRL) and disposable lenses that are designed to be used without enzyme cleaners and then discarded after a limited period of time. The build up of proteinaceous deposits may cause contact lens spoilage.

Another approach to solving the problem of protein deposits has been to try to prevent proteins from adhering to the contact lens surface in the first place. For example, U.S. Pat. No. 4,168,112 to Ellis discloses contact-lens solutions containing cationic polymers which are said to form a coating of a hydrophilic polyelectrolytic complex on the lens surface. This complex is alleged to act as a hydrogel "cushion" to increase the wettability and comfort of the lens. This complex is also said to increase the hydrophilic character of the lens and also reduce the tendency for mucoproteins to adhere to the lens surface. The examples in the patent are directed to rigid gas permeable (RGP) lenses. The patent discloses the use of polyquaternium polymers and copolymers generally, and exemplifies the immersion of a hard contact lens in a 0.1 solution of polyvinylbenzyl trimethyl ammonium chloride followed by a thorough rinse with distilled water.

Published PCT application WO 94/13774 to Powell et al. discloses a method for inhibiting the uptake of proteins by contacting a contact lens with a positively charged chemical agent having a molecular weight of 100 to 70,000. Such chemical agents include basic proteins and polypeptides such as protamine and polyarginine, both of which are said to have an average charge density greater than the average density of lysozyme, the most basic tear protein.

Missiroli et al. has found that bendazac lysine limits protein deposition on soft contacts lenses. See Missiroli, A. et al., *CLAO Journal* (Contact Lens Association of Ophthalmologists), 17(2), pp. 126–8 (April 1991). Bendazac lysine, an anti-cataract drug, is an oxyacetic acid.

The use of certain ionic polymers in contact-lens cleaning and preserving solutions is also known. For example, U.S. Pat. No. 5,096,607 and WO 94/13774 disclose the use of certain polyquaterniums as antimicrobial agents, typically in amounts less than 100 parts-per-million (ppm) in actual commercial practice. U.S. Pat. No. 4,443,429 to Smith et al. discloses the use in a contact-lens disinfecting solution of a dimethyldiallylammonium chloride homopolymer known as Merquat® 100 having a molecular weight of about 10,000 to about 1,000,000. While broad concentrations are recited in the patent, preferred concentrations are 0.0004 to about 0.02 weight percent (4 to 200 ppm). U.S. Pat. No. 4,388,229 to Fu discloses a contact-lens solution for rejuvenating lenses by removing adsorbed and occluded chemical and biological agents, particularly antimicrobial agents adsorbed from a disinfecting solution. The patent discloses the use of strongly basic anionic exchange resins having quaternary-ammonium exchange groups. After the rejuvenation procedure, the lenses may be treated with water or a cleaning and/or preserving solution to remove any residual rejuvenation solution.

Clearly, it would be desirable to be able to effectively prevent or inhibit deposition of proteins on the surface of contact lenses. It would be especially desirable to eliminate or minimize the need for special cleaning compositions or techniques to remove protein deposits from contact lenses. Finally, it would be highly desirable to eliminate or reduce the need for so-called "rubbing and cleaning." Preventing the deposition of proteinaceous materials on contact lenses in the first place would not only solve the above-mentioned problems associated with the accumulation of protein deposits, but would result in lens care becoming significantly more user-friendly and convenient. These are important attributes for many or most wearers of contact lenses.

SUMMARY OF THE INVENTION

As indicated above, traditional cleaning of contact lens involves removing protein after it has been deposited on the lens. The present invention takes an alternate approach to cleaning that involves inhibiting the deposition of protein in the first place. The present invention accomplishes this by using an ophthalmically safe composition and related methods for cleaning contact lenses. In particular, the invention is directed to certain compositions and methods used as in-the-eye and/or out-of-eye inhibitors of proteinaceous deposits on hydrophilic contact lenses. Compositions of the present invention comprise moderately charged polyquaternium polymers that selectively bind to hydrophilic contact lenses to block the binding of proteinaceous materials. In one embodiment of the invention, the composition comprises a polyquaternium copolymer that comprises a limited mole percent of net quaternary-amine-functional repeat units.

Another aspect of the invention is directed to a method of inhibiting the accumulation of protein deposits on hydrophilic contact lenses. The method comprises the steps of placing the contact lens in a solution comprising a moderately charged polyquaternium polymer that inhibits the uptake of protein. The lens is immersed (soaked or rinsed) in the solution having the polyquaternium polymer for a period of time sufficient to inhibit the formation of protein deposits on the lens.

In yet another aspect of the invention, the accumulation of protein deposits on hydrophilic lenses is prevented or inhibited by wearing contact lenses that have been conditioned by immersing the contact lens in a solution comprising a polyquaternium polymer such that the presence of the polyquaternium polymer absorbed onto the contact lens while in-the-eye inhibits the uptake and accumulation of proteinacious material and other ionic debris onto the contact lens. A contact-lens solution containing such a polyquaternium polymer can also be applied in the form of droplets while a contact lens is in the eye. The foregoing and other objects, features, and advantages of the various embodiments of the present invention will become more readily apparent from the following detailed description.

DETAILED DESCRIPTION OF THE INVENTION

The present invention is directed to the use of various moderately charged polyquaternium copolymers as in-the-eye and/or out-of-eye inhibitors of protein deposits on hydrophilic soft contact lenses. While the present invention can be used in connection with a variety of soft lenses, it is especially useful with respect to hydrophilic lenses made from polymers having repeats units derived from hydroxyethyl methacrylate monomers, and especially lenses made from polymers having additional repeat units derived from methacrylic acid. Group III and Group IV lenses (FDA categories) often contain methacrylic acid monomers. Group IV is distinguished from Groups I to III by having (with respect to Group I and III) higher water content and (with respect to Group I and II) being more ionic. Typically, Group IV lenses have a water content greater than 50% by weight. High water content is associated with materials having high oxygen permeability, resulting in the increasing popularity of Group IV lenses, including especially disposable and planned-replacement lenses. Such materials include, but are not limited to, bufilcon A, etafilcon A, methafilcon A, ocufilcon C, perfilcon A, phemfilcon A, and vifilcon A. Materials containing methacrylic acid monomers include methafilcon B, ocufilcon D, methafilcon A, and etafilcon A (USAN and the USAP Dictionary of Drug Names). Lenses made from the foregoing materials are commercially available from a variety of sources. Such lenses include daily-wear lenses, extended-wear lenses, planned-replacement lenses, and disposable lenses.

The invention comprises the use of a contact-lens solution for preventing the formation of protein deposits on a contact lens which contact-lens solution is an aqueous solution comprising an effective amount of at least one moderately charged polyquaternium polymer that binds to the lens to inhibit protein binding. By the term "moderately charged polyquaternium polymer" as used herein is meant that the polymer comprise not more than about 45 mole percent net quaternary-amine-functional repeat units, wherein the mole percent net quaternary-amine-functional repeat units are the mole percent of quaternary-amine-functional (positively charged) repeat units minus the mole percent of anionic (negatively charged) repeat units in the polymer. Preferably, the mole percent net polyquaternium repeat units is between about 10% and 45%, more preferably between about 20% and 40%, most preferably between about 25% and 35%. For example, if the polymer comprises 50 mole percent of a quaternary-amine-functional repeat unit derived from dimethyldiallyl ammonium chloride, 25 mole percent of an anionic repeat unit derived from carboxylic acid, and 25% of a neutral repeat unit derived from methyl methacrylate (or an substantially neutral repeat unit derived from hydroxyethyl methacrylate), then the mole percent net quaternary-amine-functional repeat units would be 25% (50% quaternary-amine-functional repeat units minus 25% anionic repeat units). By the term "quaternary-amine-functional repeat unit" is herein meant that the repeat unit comprises a quaternary-amine group in which a positively charged nitrogen atom is covalently bonded to four radicals (no hydrogen atoms) and ionically bonded to a negatively charged counterion such as chloride.

The polyquaternium polymers of the present invention suitably have a weight average molecular weight $M_w$ of about 5,000 to 5,000,000, preferably about 10,000 to 500,000, most preferably about 20,000 to 200,000.

The polyquaternium polymers useful in the present invention may include, but are not limited to, copolymers in which the quaternary-amine-functional repeat units are derived from one or more of the following kinds of monomers: N,N-dimethyl-N-ethyl-aminoethyl acrylate and methacrylate, 2-methacryloxyethyltrimethylammonium, N-(3-methacrylamidopropyl)-N,N,N-trimethylammonium, 1-vinyl and 3-methyl-1-vinylimidazole, N-(3-acrylamido-3-methylbutyl)-N,N,N-trimethylammonium, N-(3-methacryloyloxy-2-hydroxypropyl)-N,N,N-trimethylammonium, diallyldimethylammonium, diallyldiethylammonium, vinylbenzyltrimethylammonium, their halides or other salt forms, and derivatives thereof, for example, involving the substitution, addition, or removal of alkyl groups, preferably having 1 to 6 carbon atoms. Quaternary-amine-functional repeat units can also be obtained as a reaction product or two or more compounds, as for example, by the use of a strong alkylating agent such as 1,4-dichloro-2-butene which, for example, can be reacted with 1,4-bis[dimethylaminol]-2-butene and triethanolamine to produce a polymeric polyquartenary ammonium compound. Quaternary-amine-functional repeat units can also be made from other polymers, such as by the reaction of a trimethyl amonium substituted epoxide with the hydroxy group of a hydroxyethylcellulose. Suitable quaternary-amine-functional repeat units also include those found in polymeric ionenes and the like formed by a polycondensation reaction; in such repeat units, the nitrogens of the quaternary-amines are integral to the polymeric backbone and are situated between alkylene, oxyalkylene, or other segments.

In a preferred embodiment, the nitrogens in the quaternary-amine-functional repeat units is part of a saturated or unsaturated heterocyclic ring, most preferably a five- or six-membered ring. Most preferably, the polyquaternium polymer is a copolymer of a vinylimidazolium salt or a dimethyldiallyl ammonium salt. Up to 90%, preferably 40% to 90% by mole, of copolymerization-compatible comonomers not having a quaternary-amine-functionality may be copolymerized with the quaternary-amine-functional comonomers. Suitable comonomers include, but are not limited to, vinylpyrrolidone, acrylic acid, alkyl methacryate, amides and amines such as acrylamide and N,N-dialkylaminoalkyl acrylate and methacrylate, hydroxyethylcellulose and copolymerization-compatible mixtures thereof. A preferred alkyl group has 1 to 6 carbon atoms. Most preferably, alkyl groups are methyl, ethyl, and/or butyl.

Polyquaternium polymers as thus defined are a well known class of polymers, many variations of which are commercially available. For example, a current CTFA International Cosmetic Ingredient Dictionary includes polyquaterniums designated Polyquaternium-1 through Polyquaternium-44 a number of which, based on the present teachings, are useful in the present invention. The polymerization techniques for the preparation of such materials are similarly well known to those skilled in the art and many variations of such techniques are similarly in practice in commerce. New variations of such polyquaternium polymers are in continuous commercial development, for example, various polymers having different combinations of the same or similar repeat units, different relative proportions of comonomers, and/or different molecular weights are in continuous commercial development.

A particularly preferred polyquaternium copolymer is Luviquate® FC 370 polymer (CTFA International Cosmetic Ingredient Dictionary designation polyquaternium-16 commercially available from BASF, Ludwigshafen, Germany) which is the polymerization product of a mixture of comonomers of which 70% is vinylpyrrolidone and 30% is vinylimidazolium methochloride, commercially available as a composition with a solids content of about 40% by weight in water.

The polyquaternium copolymer is suitably present in an amount of 0.01 to 5.0 percent by weight in aqueous solution, preferably between 0.01 (100 ppm) and 1.0 percent by weight, most preferably between 200 ppm and 600 ppm. The contact-lens solution comprises 85 to 99% by weight, preferably 93 to 99% by weight, water.

The polyquaternium polymer suitably includes an ophthalmologically suitable anionic organic or inorganic counterion. A preferred counterion is chloride.

Typically, the polyquaternium polymer used in a solution according to the present invention does not increase the hydrophilic character of a lens, which means that there is no increase in the water content of the lens following treatment with the solution. The water content of a lens can be determined based on a measurement of its refractive index.

In another aspect of the present invention, selected polyquaternium polymers simultaneously satisfy the dual requirements of both (i) meeting ophthalmological safety standards for an in-the-eye contact-lens solution at concentrations of 1000 ppm and (ii) inhibiting protein binding to a contact lens. The safety requirements can be determined according to the so-called NRDR (neutral red dye release) assay for cytotoxicity described in the Examples. In particular, the polyquaternium polymer should have an NRDR assay rating of L or less at a level of 1000 ppm., preferably L or less at a level of 500 ppm (dry weight of polymer, correcting for water content of the available polymer material). The requirement for exhibiting protein-binding inhibition can be determined, at least as an initial criterion, using a test carried out as described in the Example to obtain what is herein referred to as the "SPE protein-binding inhibition." This test utilizes a particular type of Sep-Pak® solid-phase extraction cartridge identified as the Accell Plus® CM cartridge, Part #WAT020855, commercially available from Waters Corp., Milford, Mass. The material in this extraction cartridge is a weak cation exchanger that contains a silica support coated with a polymer having carboxymethyl groups. This extraction cartridge is first treated with a 1.0% solution of the polyquaternium polymer in borate-buffered saline followed by exposing the solid phase extraction cartridge to 0.05% lysozyme. The amount of protein-binding inhibition is determined compared to a control solution. In one embodiment of the invention, a suitable polyquaternium polymer exhibits at least 10% SPE protein-binding inhibition. Preferably, the SPE protein-binding inhibition is at least about 20%, more preferably at least about 30%, most preferably at least about 35%.

In another aspect of the present invention, proteinacous deposits on hydrophilic contact lenses are prevented and inhibited by a method comprising:

(a) treating the contact lens with an aqueous solution comprising a polyquaternium copolymer comprising about 10 to 45% by mole of net quaternary-amine-functional repeat units, and (b) direct installation of the treated contact lens in the eyes of the wearer.

Typically, step (a) may involve immersing the contact lens in the solution. Such immersing may comprise soaking and/or rinsing with a steady stream of the solution. Soaking may optionally comprise shaking or agitation. Preferably, step (a) involves a period of soaking the contact lens in a container wherein the contact lens is immersed in the solution. By the term "direct installation" is herein meant that the solution is not diluted or rinsed off the lens with a different contact-lens solution prior to insertion or installation in the eye.

In a particularly preferred embodiment, the method of cleaning contact lens uses a no-rub multipurpose solution without the use of an enzyme, wherein rubbing of the contact lens is neither recommended nor required. In this embodiment, the cleaning and disinfecting consists essentially of treating the contact lens with an aqueous solution comprising a polyquaternium polymer comprising about 10 to 45% by mole of net quaternary-amine functional repeat units, and then inserting the treated contact lens in the eyes of the wearer.

The present invention is also useful for packaging and storing a contact lens, the method comprising packaging a contact lens immersed in an aqueous contact-lens solution, wherein the contact-lens solution contains a polyquaternium polymer comprising about 10 to 45% by mole of net quaternary-amine-functional repeat units. Said method may comprise immersing the contact lens in an aqueous contact-lens solution prior to delivery to the customer/wearer, directly following manufacture of the contact lens. Alternately, the packaging and storing in the protein-inhibiting solution of the present invention may occur at an intermediate point before delivery to the ultimate customer (wearer) but following manufacture and transportation of the lens in a dry state, wherein the dry contact lens is hydrated by immersing the contact lens in the contact-lens solution. Consequently, a package for delivery to a customer may comprise a sealed container containing one or more unused contact lenses immersed in an aqueous contact-lens solution, wherein the contact lens solution comprises a polyquaternium copolymer comprising about 10 to 45% by mole of net quaternary-amine-functional repeat units.

Separately from, or supplementally to, immersing a contact lens in a contact-lens solution according to the present invention while the contact lens is outside the eye, the accumulation of proteins on hydrophilic contact lens can be further prevented by applying such a solution as eye drops. Thus, a ophthalmologically safe solution comprising a polyquaternium copolymer having about 10 to 45% by mole of net quaternary-amine functional repeat units can be packaged in a container adapted for applying the solution as drops to the eye.

The disinfecting solutions used with this invention will contain a disinfecting amount of one or more antimicrobial agents which are compatible. As used herein, antimicrobial agents are defined as organic chemicals which derive their antimicrobial activity through a chemical or physiochemical interaction with the microbial organisms. Suitable antimicrobial agents are polymeric quaternary ammonium salts used in ophthalmic applications such as poly [(dimethyliminio)-2-butene-1,4-diyl chloride], [α-tris(2-hydroxyethyl) ammonio]-2-butenyl-ω-[tris(2-hydroxyethyl) ammonio]dichloride (chemical registry number 75345-27-6) generally available as polyquaternium 1 from ONYX Corporation, benzalkonium halides, and biguanides such as salts of alexidine, alexidine free base, salts of chlorhexidine, hexamethylene biguanides and their polymers. The antimicrobial agents used herein are preferably employed in the absence of mercury-containing compounds such as thimerosal. The salts of alexidine and chlorhexidine can be either organic or inorganic and are typically gluconates, nitrates, acetates, phosphates, sulphates, halides and the like. Preferred antimicrobal agents are the polymeric quaternary ammonium salts used in ophthalmic applications and the biguanides. More preferred are the biguanides and hexamethylene biguanides (commercially available from Zeneca, Wilmington, Del.), their polymers and water-soluble salts being most preferred. Generally, the hexamethylene biguanide polymers, also referred to as polyaminopropyl biguanide (PAPB), have molecular weights of up to about 100,000. Such compounds are known and are disclosed in U.S. Pat. No. 4,758,595 which patent is incorporated herein be reference.

A disinfecting amount of antimicrobial agent is an amount which will at least partially reduce the microorganism population in the formulations employed. Preferably, a disinfecting amount is that which will reduce the microbial burden by a certain number of log orders within a certain period of time, depending on the particular microorganism involved. Most preferably, a disinfecting amount is an amount which will eliminate the microbial burden on a contact lens when used in regimen for the recommended soaking time (FDA Chemical Disinfection Efficacy Test—July, 1985 Contact Lens Solution Draft Guidelines). Typically, such agents are present in concentrations ranging from about 0.00001 to about 0.5% (w/v), and more preferably, from about 0.00003 to about 0.5% (w/v).

Compositions of the present invention, in addition to the active ingredients described above, may contain buffers, various cleaners, stabilizers, isotonic agents and the like which aid in making ophthalmic compositions more comfortable to the user. The aqueous solutions of the present invention are typically adjusted with tonicity agents to approximate the osmotic pressure of normal lacrimal fluids which is equivalent to a 0.9% solution of sodium chloride or 2.5% of glycerol solution. The solutions are made substantially isotonic with physiological saline used alone or in combination, otherwise if simply blended with sterile water and made hypotonic or made hypertonic the lenses will lose their desirable optical parameters. Correspondingly, excess saline may result in the formation of a hypertonic solution which will cause stinging and eye irritation. An Osmolality of about 225 to 400 mOsm/kg is preferred.

The solutions of the present invention may be formulated into specific contact lens care products, such as wetting solutions, soaking solutions, cleaning and conditioning solutions, as well as multipurpose type of lens-care solutions, etc. and mixtures thereof When used in a cleaner, neutral or non-ionic surfactants may impart additional cleaning and conditioning properties and are usually present in amounts up to 15 weight percent. The surfactant should be soluble in the lens care solution, non-irritating to eye tissues and usually have a hydrophilic-lipophile balance (HLB) of 12.4 to 18.8. Satisfactory non-ionic surfactants include polyethylene glycol esters of fatty acids, e.g. coconut, polysorbate, polyoxyethylene or polyoxypropylene ethers of higher alkanes ($C_{12}$–$C_{18}$). Examples of the preferred class include polysorbate 20 (available from ICI Americas Inc., Wilmington, Del. 19897 under the trademark Tween 20), polyoxyethylene (23) lauryl ether (Brij® 35), polyoxyethylene (40) stearate (Myth 52), polyoxyethylene (25) propylene glycol stearate (Atlas® G 2612). Brij® 35, Myrj® 52 and Atlas® G 2612 are trademarks of, and are commercially available from, ICI Americas Inc., Wilmington, Del. 19897.

One non-ionic surfactant in particular, consisting of a poly(oxypropylene)-poly(oxyethylene) adduct of ethylene diamine having a molecular weight from about 7,500 to about 27,000 wherein at least 40 weight percent of said adduct is poly(oxyethylene), has been found to be particularly advantageous for use in cleaning and conditioning contact lenses when used in amounts from about 0.01 to about 15 weight percent. The CFTA Cosmetic Ingredient Dictionary's adopted name for this group of surfactants is poloxarnine. Such surfactants are available from BASF Wyandotte Corp., Wyandotte, Mich., under the registered trademark "Tetronic". An analogous series of surfactants is the poloxamer series which is a polyoxyethylene, polyoxypropylene block polymer available from BASF Wyandotte Corp., Parsippany, N.J. 07054 under the trademark "Pluronlc".

Amphoteric, polyquaternium and nonionic surfactants suitable for use in the invention can be readily ascertained, in view of the foregoing description, from McCutcheon's Detergents and Emulsifiers, North American Edition, McCutcheon Division, MC Publishing Co., Glen Pock, N.J. 07452.

It may also be desirable to include water-soluble viscosity builders in the solutions of the present invention. Because of their demulcent effect, viscosity builders have a tendency to enhance the lens wearer's comfort by means of a film on the lens surface cushioning impact against the eye. Included among the water-soluble viscosity builders are the cellulose polymers like hydroxyethyl or hydroxypropyl cellulose, and the like. Such viscosity builders may be employed in amounts ranging from about 0.01 to about 4.0 weight percent or less.

In addition to the active ingredients previously described, tonicity agents, buffers and sequestering agents may be optionally employed. In this regard, added materials must be non-toxic and must not distort the lens.

In order to maintain the pH of the cleaning and conditioning solutions within the range of 3.0 to 9.0, preferably 5.0 to 8.0, more preferably about 6.0 to 8.0, most preferably about 6.5 to 7.8, suitable buffers may be added, such as boric acid, sodium borate, potassium citrate, citric acid, sodium bicarbonate, TRIS, and various mixed phosphate buffers (including combinations of $Na_2HPO_4$, $NaH_2PO_4$ and $KH_2PO_4$) and mixtures thereof Borate buffers are preferred. Generally, buffers will be used in amounts ranging from about 0.05 to 2.5 percent (w/v), and preferably, from 0.1 to 1.5 percent (w/v).

In addition to buffering agents, in some instances it may be desirable to include sequestering agents in the cleaning and conditioning solutions in order to bind metal ions which might otherwise react with the lens and/or protein deposits and collect on the lens. Ethylene-diaminetetraacetic acid (EDTA) and its salts (disodium) are preferred examples. They are usually added in amounts ranging from about 0.01 to about 0.2 weight percent.

The aqueous cleaning and conditioning solutions may be effectively used in removing and dispersing protein and lipid tear film deposits on soft type contact lenses by ally of the well-recognized methods. For example, when the wearer of contact lenses removes them from the eyes, the lens may be rinsed with the cleaning solution followed by "cold" soaking at room temperature for a period ranging from about five minutes to sixteen hours, preferably five minutes to 4 hours. The lenses are then removed from the solution, rinsed with a preserved isotonic saline solution and then replaced on the eyes.

The cleaning and rinsing solution may be the same when, for example, the cleaning solution is a multipurpose formulation, for example, that contains limited amounts of a surfactant in accordance with commonly assigned U.S. Pat. No. 4,820,352, hereby incorporated by reference in its entirety. In addition to the cold soaking method, the solutions disclosed herein are adaptable for use in other types of equipment such as ultrasonic cleaners. Furthermore, because the solutions are also stable when heated to temperatures in the range of 80° to 90° C., they are also adaptable for use with high temperature disinfecting methods. Typically, lenses are heated to 80° C. in a disinfecting unit containing cleaning and conditioning solutions for a time period of at least 10 minutes, removed and rinsed with isotonic saline.

In one embodiment of the present invention, a composition of the present invention can be used with a planned replacement lens (PRL) that is planned for replacement after a period of use between 1 and 4 weeks, for example, 2 weeks. Preferably, the lens is made from a polymer comprising about 0.5 to 5 mole percent repeat units derived from methacrylic acid (MAA), 10 to 99 mole percent of repeat units derived from hydroxyethyl methacrylate, and about 0.5 to 5 mole percent of cross-linking repeat units. Cross-linking repeat units may be derived, for example, from such monomers as ethyleneglycol dimethacrylate, divinylbenzene, and trimethylpropane trimethacrylate. In this embodiment, a composition according to the present composition can be used as a multipurpose solution that eliminates the requirement for a supplemental protein cleaner. Preferably, the composition can be used as a multipurpose solution that also eliminates the requirement for any daily "rubbing and cleaning/rinsing" of the lenses.

The following specific experiments and examples demonstrate the compositions and methods of the present invention. However, it is to be understood that these examples are for illustrative purposes only and do not purport to be wholly definitive as to conditions and scope.

EXPERIMENT 1

This Experiment illustrates the measurement of the protein-displacing effects of various polyquaternium polymers. Among the polyquaternium polymers tested, the polymers varied with respect to the comonomers making up the polymer, the respective proportion of comonomers, and/or the molecular weight of the polymer. The following screening procedure was used. Cartridges were used containing solid-phase extraction (SPE) resin, namely Sep-Pak® cartridges identified as Accell Plus® CM Cartridges, 3 cc in size, part no. WAT020855, available from Waters Corp., Milford, Mass. The material used to pack the cartridge is a silica-based, hydrophilic, weak cation exchanger with large pore size. The silica support is coated with a polymer having carboxymethyl groups. For the purpose of measuring the inhibition of protein binding, the material used to pack the cartridge has been found to be similar to Group III or IV lens material. The SPE cartridges were first conditioned with 3 mL borate buffered Sine (BBS) containing (by w/v) 0.85% boric acid, 0.45% NaCl, 0.09% sodium borate, q.s. to 100% water, pH 7.2, 290 mOsm/kg. The SPE cartridges were then treated with 3 mL of test solutions (typically 1% active in BBS). The various test solutions are listed in Table 2 below. The SPE cartridges were subsequently rinsed with 3 mL of BBS and then treated with 3 mL of 0.05% lysozyme (3X crystallized hen lysozyme from Sigma Chemical Corp.) in electrolyte solution, adjusting pH if necessary to 7.2+/−0.1 with HCl or NaOH. The electrolyte solution contained (by w/v) 0.70% sodium chloride, 0.17% potassium chloride, 0.22% sodium bicarbonate, and 0.0005% calcium chloride dihydrate, dissolved in approximately 90% volume of distilled water, adjusting to pH 7.2+/−0.1 using 1N HCl or 1N NaOH and bringing to volume with distilled water and mixing. Each solution was introduced into a cartridge using a 5 mL disposable syringe employing a Varian™ Bond Elute Syringe Adapter, part # 803227. After removing the syringe adapter, introducing solution into the syringe, and replacing the plunger consistent pressure was used to force the solution through the cartridge. Once the plunger reached the bottom of the syringe, it was held down for approximately two seconds until the pressure equalized and the solution was entirely eluted. If foaming occurred with any solution, the plunger was held down until foaming stopped. The eluent was collected and the absorbance determined at 280 nm, in order to determine (with a UV spectrophotometer, Shimadzu model #UV-160) the amount of lysozyme that bound to the column (the less bound, the more effective the test solution). The absorbance measurements were conducted by (1) taking an initial absorbance with BBS in a 1 cm cuvette, which reading should be 0.000, re-autozeroing if necessary with BBS, (2) rinsing and filling the cuvette with 0.05% lysozyme solution and reading the absorbance to obtain the "maximum inhibition value', and (3) reading the absorbances for the solutions in the test tubes used to collect the eluents from the test cartridges. The corrected absorbances for the test solutions were obtained by subtracting the absorbance of a control in which the cartridge was treated with 3 mL of BBS. (The absorbance of the control was used to account for any residual sample which may absorb at 280nm.) The percent SPE protein-binding inhibition (% Inh. or % SPE Binding Inhibition) is obtained by dividing each corrected test absorbance by the maximum inhibition value and multiplying by 100. The results are shown in the following Table 1.

TABLE 1

| Trial | Test Compounds* (1% in BBS) | Average % SPE Binding Inhibition |
|---|---|---|
| 1 | Luviquat ® FC 370 polyquaternium-16 (30% cationic) | 48 |
| 2 | Luviquat ® 550 polyquaternium-16 (50% cationic) | 36 |
| 3 | Luviquat ® 552 polyquaternium-16 (50% cationic) | 34 |
| 4 | Merquat ® 280 polyquaternium-22 (80% cationic, 20% anionic) | 50 |
| 5 | Merquat ® 295 polyquaternium-22 | 38 |
| 6 | Merquat ® 2200 polymer | 41 |
| 7 | Luviquat ® 905 polyquaternium-16 (90% cationic) | 29 |
| 8 | Merquat ® 100 polyquaternium-6 (100% cationic) | 31 |
| 9 | Merquat ® 3330 polyquaternium-39 (50% cationic, 25% anionic) | 25 |
| 10 | Merquat ® 3331 polyquaternium-39 | 25 |
| 11 | Quadrol Polyol tetrahydroxypropyl ethylene-diamine | 8 |
| 12 | Ritaquat ® 3000 polyquaternium-10 | 6 |
| 13 | Ritaquat ® 400 KG polyquaternium-10 | 17 |
| 14 | Polymer JR ® polyquaternium-10 | 27 |
| 15 | Gluquat ® 125 lauryl methyl gluceth-10 hydroxy-propyl dimonium chloride | 2 |
| 16 | Crodacel ® QM cocodimonium hydroxypropyl oxyethyl cellulose | 10 |
| 17 | BAK (benzalkonium chloride) | 3 |
| 18 | BAB (benzalkonium bromide) | 8 |
| 19 | Agequat ® 500 polyquaternium-7 | 8 |
| 20 | Agequat ® 5008 polyquaternium-7 | 13 |
| 21 | Busan ® 1507 polyquaternium-42 | 60 |
| 22 | Polyquart ® H PEG-15 cocopolyamine polyimidazoline quaternized) | 29 |
| 23 | Gafquat ® 734 polyquaternium-11 | 46 |
| 24 | Gafquat ® HS100 polyquaternium-28 | 27 |

*Luviquat ® is a registered trademark of BASF Aktiengesellschaft, Ludwigshafen, Germany, Merquat ® is a registered trademark of Calgon Corp., Pittsburgh PA 15230, Ritaquat is a registered trademark of Rita Corp., Gluquat ® is a registered trademark of Amerchol Corp., Crodacel ® is a registered trademark of Croda Corp., BAK and BAB are commerically available from Sigma Corp., Quadrol Polyol ® is commerically available from BASF, Agequat ® is a registered trademark of CPS Corp., Busan ® is a registered trademark of Buckman Corp., Polyquart ® is a registered trademark of Henkel Scientific Polymers Corp., and Gafquat ® is a registered trademark of ISP Corp.

The results in Table 1 show that Luviquat® 370, Luviquat® 550, Merquat® 280, Merquat® 2200 and other polymers showed greater than about 35% SPE protein-binding inhibition. Most preferably, the binding inhibition of polyquaternium polymers used in the present invention should exhibit, according to this screening test, an SPE protein-binding inhibition of about 35% or above. For use in the present invention, however, the polymer must also meet the requirement for ophthalmic safety (evidenced by the NRDR assay) such that, at a concentration greater than 100 ppm, the polymer can be used in a contact-lens solution intended for coating the lens when placed in the eye.

EXPERIMENT 2

This Example further illustrates the use of a composition according to the present invention for inhibiting protein deposition on hydrophilic contact lenses. Various polyquaternium polymers were added to a ReNu® MPS base formulation (manufactured by Bausch & Lomb, Rochester, N.Y.) and subjected to various cleaning cycles with Group IV lenses (Acuvue manufactured by Johnson & Johnson, New Brunswick, N.J.). In particular, the lenses were alternately exposed to various concentrations of the polyquaternium solution followed by protein (lysozyme) solutions. The protein solution was prepared by dissolving 0.1% lysozyme in the electrolyte solution described in Experiment 1. Cleaning was determined as a percent difference in the amount of lysoyme deposited on test solution lenses versus ReNu MPS control lenses. Protein deposition was determined using a ninhydrin total protein assay adapted for contact lenses according to the following method for the evaluation of cleaning.

Cleaning Evaluation

A modified ninhydrin test procedure (for more information regarding ninhydrin procedures, see Shibata and Matoba, "Modified Colorimetric Ninhydrin Methods for Peptidase Assay," *Analytical Biochemistry* 1981; 118:173–184,) was used to determine the amount of proteinaceous material removed from the lenses using various cleaning solutions described below. The procedure was substantially as follows: After being treated with a cleaning solution, each lens was subsequently cut into quarters and the four quarters where placed into a glass test tube. The protein bound to each lens was hydrolyzed by adding 1 mL of 2.5N sodium hydroxide to each tube such that the individual lens pieces therein were completely covered with the base solution. The tubes were capped, placed into a preheated heating block (about 100° C.) for approximately two hours, and then removed from the block. The tubes were allowed to cool to room temperature (minimum 30 minutes, not to exceed four hours with lens pieces still in solution) and a 15 $\mu$L aliquot of contact lens hydrolysate (hydrolyzed protein from the lens) was removed from each tube, diluted in a 1 to 10 ratio (by volume) with 2.5N sodium hydroxide and subsequently placed into individual disposable polystyrene culture tubes. These culture tubes were subsequently sealed and the contents mixed. Glacial acetic acid in the amount of 50 $\mu$L was added to each tube to neutralize the sodium hydroxide. Subsequently, 400 $\mu$L of a ninhydrin reagent (described below) was added to each tube and mixed thoroughly. The tubes were then capped and heated in a water bath (or heating block) at about 90° C. for approximately 20 minutes. The tubes were immediately transferred to an ice bath to cool for approximately 5 minutes. Upon cooling, 1.0 mL of an equal volume solution of isopropyl alcohol and distilled water was added to each tube. The mixture within the tubes was then thoroughly mixed and the absorbance of each tube was measured at 570 nm on an ultraviolet spectrophotometer.

The amount of protein in each sample was calculated by comparing the absorbance of each sample to that of a known phenylalanine standard curve. The phenylalanine standard curve was prepared by using a working standard of 0.1 mg/mL phenylalanine solution in a disposable polystyrene culture tube. Appropriate dilutions were made to give a range of concentration from about 0 µg to 15 µg. The phenylalanine solution was prepared by dissolving 0.1% (1 mg/mL) phenylaanine into 2.5N sodium hydroxide and stirring for approximately 10 minutes.

The ninhydrin reagent used in the procedure was prepared by dissolving 1.0% ninhydrin and 0.1% stannous chloride into an appropriate amount of methyl cellosolve (ethylene glycol, monomethyl ether) that will yield 50% of the total volume. This mixture was stirred until the solids dissolved into solution. A citrate-acetate buffer was then added to bring the solution up to 100%. The citrate-acetate buffer was prepared by dissolving about 28.6 mL of acetic acid and 21.0 g of citric acid in approximately 850 mL of distilled water. The solution was then mixed and the pH was adjusted to about 5.0 with an appropriate base (e.g., 10N sodium hydroxide). The volume of the solution was then brought up to approximately 1 L with distilled water.

The cleaning results reported in Table 2 below are indicated as a percentage improvement in protein inhibition as compared with a substantially identical cleaning treatment utilizing only the ReNu® MPS control solution.

TABLE 2

In Vitro Cleaning Efficacy Results for
Luviquat ® FC 370 in ReNu ® MPS Solution

| Solution | No. of Lenses | No. of Cycles | Protein Exposure Conditions | Treatment Exposure Conditions | Presoak w/Cationic Polymer | % Cleaning vs. Control |
|---|---|---|---|---|---|---|
| 1% Luviquat ® 370 System | 6 | 7 | 1 hr/37° C. | 3 hr/r.t. | Yes | 90 |
| 1% Luviquat ® 370 System | 9 | 4 | 20 hr/37° C. | 4 hr/r.t. | Yes | 79 |
| 1% Luviquat ® 370 System | 6 | 4 | 20 hr/37° C. | 4 hr/r.t. | No | 57 |
| 0.1% Luviquat ® 370 System | 6 | 4 | 20 hr/37° C. | 4 hr/r.t. | Yes | 30 |
| 1% Merquat ® 280 System | 8 | 7 | 1 hr/37° C. | 3 hr/r.t. | Yes | 74 |
| 1% Merquat ® 280 System | 6 | 4 | 20 hr/37° C. | 4 hr/r.t. | No | 25 |
| 1% Merquat ® 280 System | 9 | 4 | 20 hr/37° C. | 4 hr/r.t. | Yes | 35 |
| 0.1% Merquat ® 280 System | 6 | 4 | 20 hr/37° C. | 4 hr/r.t. | Yes | −7 |

These results show that the solution containing Luviquat® 370 polymers demonstrated, even under extreme deposition conditions, the ability to significantly reduce the amount of lysozyme (protein) depositing on Group IV lenses. For example, the 1% Luviquat® 370 solution showed 79% less protein absorbed after four of the cationic/lysozyme cycles with 20 hours exposure to protein in each cycle. Again, however, for use in the present invention, the polymer must also meet the requirement with respect to safety according to cytotoxicity testing such that, at a concentration greater than 100 ppm, the polymer can be used in a contact-lens solution intended for coating the lens when placed in the eye.

EXAMPLE 1

This example illustrates one embodiment of the present composition for inhibiting protein deposition on contact lens. The components of the composition are as follows:

TABLE 3

| Ingredient | mg/gm | % w/w |
|---|---|---|
| Polyhexamethylene Biguanide HCl (as Cosmocil ® CQ) (20% w/w solution PAPB) | 0.009 | 0.0009 |
| Boric Acid | 6.6 | 0.66 |
| Sodium Borate | 1.0 | 0.1 |
| Edetate Disodium | 1.0 | 0.1 |
| Sodium Chloride | 4.9 | 0.49 |
| Poloxamine 1107 | 10.0 | 1.0 |
| Luviquat ® FC 370 polymer (40% w/w solution active ingred.) | 1.0* | 0.1** |
| Hydrochloric Acid, 1N | adjust to pH 7.1–7.4 | |
| Sodium Hydroxide, 1N | adjust to pH 7.1–7.4 | |
| Purified Water, qs to | 1.00 gm | 100% |

*Prepare as Luviquat ® FC 370, do not adjust for % active

To a stainless steel vessel is added purified water to approximately 85% of total batch weight. The vessel is then placed on a hot plate equipped with a mixer, and the solution is warmed to approximately 60° C. with mixing. The salts are added one at a time, making sure that each is dissolved before adding the next salt. The heat is then turned off and Poloxamine 1107 is added with constant mixing. The Luviquat® FC 370 polymer is added and mixed to dissolve. The solution, after optional autoclaving, is allowed to cool and a PAPB concentrate (approx. 100 ppm) is added and qs to the desired weight with water. The pH and osmolality of the formulation if measured and adjusted to a pH of 7.2 +/−0.1 if necessary.

EXAMPLE 2

This example illustrates the safety requirements of a suitable polyquaternium compound for use in the present invention. An in vitro evaluation of cytotoxicity to a cultured mamalian cell line is used to measure the potential ocular compatibility of an ingredient in solution. The United States Pharmacopeia specifies the Agar Diffusion Test as a preliminary evaluation of potentially toxic substances extracted from elastomeric (plastic) materials preceding subsequent in vivo toxicity testing. The principle of the Agar Diffusion Test was made into a quantitative assay known as the Neutral Red Dye Release (NRDR) assay for the evaluation of contact-lens disinfecting/preservative formulations. In this method, cultured mamalian cells are loaded with the non-toxic dye Neutral Red, which is retained in the intracellular compartment by each cell's plasma membrane, a lipid sack which contains the cell's contents and permits selective passage of nutrients, wastes and other substances. Upon exposure to test solutions, the rate and extent of plasma membrane permeablization is measured by the amount of dye released into the solution. This loss of membrane integrity is used as a measure of potential ocular toxicity mediated by solution ingredients. The term "NRDR assay," as used herein, refers to the Modified Neutral Red Dye Release (NRDR) Assay, or its essential equivalent, described in detail by Hamberger, J. F. et al., "The Relative Toxicity of Five Common Disinfecting/Preserving Agents as Determined by a Modified Neutral Red Dye Release Assay and the Agar Overlay Technique," *ICLC*, Vol. 1 at 130–35 (May/June 1992), except that samples after exposure are taken at 30 minute intervals for a total of 90 minutes. Using such an assay, in which various samples were prepared, the results shown in Table 4 below were obtained. The rating system is based on the Percent (%) of total cellular dye release after 90 minutes of exposure as follows:

0 =No cytotoxicity observed (0–10%)

L=Low cytotoxicity (10–20%)

M=Medium Cytotoxicity (20–30%)

H=High Cytotoxicity (30–40%)

VH=Very High Cytotoxicity (greater than 40%)

As used herein, the term "NRDR assay rating" refers to the latter rating system applied to the results of an NRDR assay. Only a polymer that exhibited a rating of 0 or L (low) at 1000 ppm is acceptable for use in the present invention.

TABLE 4

| Sample (polyquat) | NRDR Sol'n Rating |
| --- | --- |
| 400 ppm Luviquat ® 370 solution | L |
| 120 ppm Luviquat ® 370 solution | 0 |
| 1000 ppm Merquat ® 3330 | 0 |
| Borate Buffer Control solution | 0 |

Luviquat® 370 polymer has 30% mole percent net quaternary-amine-functional repeat units. Thus, this shows that a moderately charged polyquaternium polymer surprisingly exhibits both superior protein-binding inhibition (as shown in previous Experiment 1 and 2) and meets the safety standard according to the present cytotoxicity test procedure.

COMPARATIVE EXAMPLE 3

This example compares the cytotoxicity of various polyquaternium compounds not usable in the present invention. For such a comparison, the same assay and rating system is utilized as described in Example 2 above. Using such an assay, in which various samples were prepared, the results shown in Table 5 below were obtained.

TABLE 5

| Sample | NRDR Sol'n Rating |
| --- | --- |
| 400 ppm Luviquat ® 550 | VH |
| 200 ppm Luviquat ® 552 | VH |
| 400 ppm Luviquat ® 905 | VH |
| 4000 ppm Merquat ® 280 | VH |
| 400 ppm Merquat ® 280 | H |
| 40 ppm Merquat ® 280 | 0 |

TABLE 5-continued

| Sample | NRDR Sol'n Rating |
| --- | --- |
| 4 ppm Merquat ® 280 | 0 |
| BBS Control | 0 |

All the samples concentrations are corrected for water content, for example, 1000 ppm of a polymer material comprising 40% water represents polymer in the amount of 400 ppm. The polyquaternary polymers in Table 5 comprised 50% or more not quaternary-amine-functional repeat units, indicating that such highly charged or strongly basic polymers generally do not meet the requirements for use in the present invention.

What is claimed is:

1. An aqueous contact-lens solution for preventing the formation of protein deposits on a contact lens which contact-lens solution is an aqueous solution comprising an effective amount of at least one polyquaternium polymer having a weight average molecular weight of 5,000 to 5,000,000 comprising about 10 to 45 mole percent of net quaternary-amine-functional repeat units.

2. The contact-lens solution of claim 1, wherein the polyquaternium copolymer is characterized by at least about 10% SPE protein-binding inhibition.

3. The contact-lens solution of claim 1, comprising 93 to 99% by weight water.

4. The contact-lens solution of claim 1 further comprising an ophthalmologically suitable salt.

5. The contact-lens solution of claim 4 wherein the ophthalmologically suitable salt is selected from the group consisting of an alkali metal or alkaline earth metal halide salt.

6. The contact-lens solution of claim 1, wherein said polyquaternium polymer is present in an amount of between 0.01 to 5.0 percent by weight.

7. The contact-lens solution of claim 1 wherein said polyquaternium copolymer comprises about 20 to 40 percent by mole net quaternary-amine-functional repeat units.

8. The contact-lens solution of claim 1, wherein the quaternary-amine-functional repeat units comprise a positively charged nitrogen atom that is part of a saturated or unsaturated heterocyclic ring.

9. The contact-lens solution of claim 8, wherein the polyquaternium polymer is a copolymer of a comonomer selected from the group consisting of substituted or unsubstituted vinylimidazole or vinylimidazolium salts, dimethyldiallyl ammonium salts, 2-methacryloyloxyethyltrimethylammonium salts, and copolymerization-compatible mixtures thereof.

10. The contact lens solution of claim 1 wherein the polyquaternium copolymer is a copolymer of up to 90 mole percent of a comonomer selected from the group consisting of vinylpyrrolidone, acrylamide, acrylic acid, methyl methacryate, and copolymerization-compatible mixtures thereof.

11. The contact lens solution of claim 1 having a pH of 6 to 8.

12. A package system comprising a sealed container containing one or more unused contact lens immersed in an aqueous contact-lens solution, wherein the contact lens solution comprises a polyquaternium copolymer having a weight average molecular weight of 5,000 to 5,000,000 and comprising about 10 to 45 mole percent of net quaternary-amine-functional repeat units.

* * * * *